(12) United States Patent
Wang et al.

(10) Patent No.: US 9,504,256 B2
(45) Date of Patent: Nov. 29, 2016

(54) FABRICATION OF MAGNETIC NANOPARTICLES

(71) Applicants: Lei Wang, Columbia, SC (US); Brian Benicewicz, Columbia, SC (US)

(72) Inventors: Lei Wang, Columbia, SC (US); Brian Benicewicz, Columbia, SC (US)

(73) Assignee: University of South Carolina, Columbia, SC (US)

( * ) Notice: Subject to any disclaimer, the term of this patent is extended or adjusted under 35 U.S.C. 154(b) by 138 days.

(21) Appl. No.: 14/489,587

(22) Filed: Sep. 18, 2014

(65) Prior Publication Data

US 2015/0079270 A1   Mar. 19, 2015

Related U.S. Application Data (60) Provisional application No. 61/879,184, filed on Sep. 18, 2013.

(51) Int. Cl.
| | | |
|---|---|---|
| *A01N 59/16* | (2006.01) | |
| *A01N 25/26* | (2006.01) | |
| *A01N 43/90* | (2006.01) | |
| *A01N 63/04* | (2006.01) | |

(52) U.S. Cl.
CPC .............. *A01N 59/16* (2013.01); *A01N 25/26* (2013.01); *A01N 43/90* (2013.01); *A01N 63/04* (2013.01)

(58) Field of Classification Search
CPC combination set(s) only.
See application file for complete search history.

(56) References Cited

U.S. PATENT DOCUMENTS

2012/0302700 A1   11/2012   Tao et al.
2013/0041112 A1   2/2013   Benicewicz et al.

FOREIGN PATENT DOCUMENTS

WO   WO 2013/078309   5/2013

OTHER PUBLICATIONS

Yang et al, Journal of Materials Chemistry, 22, pp. 25354-25361, published Oct. 11, 2012.*
He et al, JACS, 134, pp. 11342-11345, published Jul. 2, 2012.*
Wang et al., "Synthesis and Characterization of Dye-Labeled Poly(methacrylic acid) Grafted Silica Nanoparticles", ACS Macro Letters 2, 2013, 173-176.

* cited by examiner

*Primary Examiner* — Erma Cameron
(74) *Attorney, Agent, or Firm* — Dority & Manning, P.A.

(57) ABSTRACT

Methods for forming core-shell magnetic nanoparticles are provided. The method can include: forming an oxide shell around a metal oxide core to form a core-shell magnetic nanoparticle; attaching an anchoring agent to the magnetic nanoparticle; reacting a RAFT agent with the functional group of the anchoring agent such that the RAFT agent is bonded to the magnetic nanoparticle through the anchoring agent; and attaching a polymeric chain to the RAFT agent.

17 Claims, 5 Drawing Sheets

FABRICATION OF MAGNETIC NANOPARTICLES

RELATED APPLICATION

The present application claims priority to U.S. Provisional Patent Application Ser. No. 61/879,184 filed on Sep. 18, 2013 of Wang, et al. titled "Fabrication of Magnetic Nanoparticles," which is incorporated by reference herein.

BACKGROUND

Nanomaterials have been widely used in various areas due to the unique properties. Magnetic nanoparticles can be applied in many industries, such as biomedical, magnetic identification and data-storage systems, depending on the size and magnetic properties. More specifically, magnetic nanoparticles can be used as contrast agents in MRI by using the interaction between magnetic field and hydrogen nucleus. Magnetic nanoparticles can also be used as a local heater to kill tumor cells under magnetic field with a certain frequency. Magnetic nanoparticles with long relaxation times can be used as information recorder in data-storage field.

More specifically, magnetic nanoparticles with controlled size and high magnetization, are demonstrated as important materials with wide applications in magnetic recording, magnetic resonance imaging (MRI), drug delivery and therapy. However, there are many problems of the application of bare iron oxide nanoparticles, such as easy aggregation, quick biology-caused decomposition and the further loss of the magnetic property. Silica coated iron oxide core-shell structure magnetic nanoparticles provide the protecting biocompatible silica shell, which is also a platform for subsequent surface functionalization via a powerful silica surface chemistry toolbox.

There are several traditional methods to prepare the iron oxide/silica shell magnetic nanoparticles, namely coprecipitation of Fe(II), Fe(III) salts and tetraethyl orthosilicate (TEOS) in microemulsion or thermal decomposition of Fe(III) chelate under high temperature resulting in iron oxide nanoparticle seed followed by hydrolysis of TEOS on the particle surfaces. The first strategy usually generates magnetic nanoparticles with poor magnetization which cannot meet the needs for real applications. The second method requires harsh condition: high temperature (at least above 200° C., usually around 265° C.), which is an obstacle for its scale-up fabrication in industry. It is also known that the magnetization values are critically dependent on the size of the nanoparticle with lower values being measured at smaller sizes. Thus, it is a challenge to prepare nanoparticles with small sizes and high magnetization values.

As such, a need exists for a method of forming magnetic nanoparticles under mild conditions suitable for scale-up fabrications in industrial uses, while still resulting in high saturation magnetization.

SUMMARY

Objects and advantages of the invention will be set forth in part in the following description, or may be obvious from the description, or may be learned through practice of the invention.

Methods are generally provided for forming core-shell magnetic nanoparticles. In one embodiment, the method includes: forming an oxide shell around a metal oxide core to form a core-shell magnetic nanoparticle; attaching an anchoring agent to the magnetic nanoparticle; reacting a RAFT agent with the functional group of the anchoring agent such that the RAFT agent is bonded to the magnetic nanoparticle through the anchoring agent; and attaching a polymeric chain to the RAFT agent.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale up to about 100 nm. For example, particles having an average diameter on the nanometer scale (e.g., from about 0.1 nm to about 100 nm) are referred to as "nanoparticles."

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\sum_i N_i M_i}{\sum_i N_i}$$

where $N_i$ is the number of molecules of molecular weight $M_i$. The number average molecular weight of a polymer can be determined by gel permeation chromatography, and all colligative methods, like vapor pressure osmometry or end-group determination.

The "weight average molecular weight" ($M_w$) is readily calculated by one of ordinary skill in the art, and generally refers to:

$$\overline{M}_w = \frac{\sum_i N_i M_i^2}{\sum_i N_i M_i}$$

where $N_i$ is the number of molecules of molecular weight $M_i$. The weight average molecular weight can be determined by light scattering, small angle neutron scattering (SANS), gel permeation chromatography, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally provided for the formation of controlled size magnetic nanoparticles (e.g., iron oxide/silica core-shell magnetic nanoparticles) with an extremely high saturation magnetization under mild operation conditions, which is extremely significant for scale-up fabrications for industry uses. Additionally, methods are generally provided for direct surface-initiated RAFT polymerization to prepare fluorescent PMAA grafted magnetic nanoparticles, which is much easier than traditional methods requiring multi-steps harsh chemical process. The multi carboxylic acid moieties provide an important and classic organic synthesis precursor for post functionalization with targeting compounds, such as antibiotics, SiRNA, recognition groups. The fluorescent PMAA grafted magnetic nanoparticles provides a great universal platform for biomedical applications, such as magnetic resonance imaging (MRI), drug delivery and therapy.

In one embodiment, a method is generally provided for forming a core-shell magnetic nanoparticle by (1) forming an oxide shell around a metal oxide core to form the magnetic nanoparticle; (2) attaching an anchoring agent to the magnetic nanoparticle; (3) reacting a RAFT agent with a functional group of the anchoring agent such that the RAFT agent is bonded to the magnetic nanoparticle through the anchoring agent; and (4) polymerizing a plurality of monomers on the RAFT agent to form a polymeric chain covalently bonded to the magnetic nanoparticle via the RAFT agent.

Each of these steps is discussed in greater detail below.

I. Formation of Core-Shell Magnetic Nanoparticles

The core-shell nanoparticles are generally formed under mild conditions suitable for scale-up fabrications for industry uses. The technology generates controlled size iron oxide/silica core-shell magnetic nanoparticles with an extremely high saturation magnetization under mild operation conditions.

In one embodiment, metal salts are first precipitated in a solvent in the presence of a base (e.g., ammonium hydroxide ($NH_4OH$), potassium hydroxide (KOH), sodium hydroxide (NaOH), etc) at mild temperatures. For example, the solvent can include water, with ammonia present to form $NH_4OH$. Ammonia can be present in a concentration up to about 0.5 g/mL, such as about 0.01 g/mL to about 0.1 g/mL, or such as about 0.025 g/mL to about 0.05 g/mL (e.g., about 0.033 g/mL). In particular, the molar ratio between ammonia to iron salts can be about 5 to about 7.5 (e.g, about 6:1, such as about 6.084:1). Generally, the metal salts react with the hydroxyl group of the ammonium hydroxide to form a metal oxide particle. For example, when the metal salts include iron salts, such as Fe(III) salts, Fe(II) salts, or a mixture thereof, then iron oxide particles are formed. Although described with particular reference to ammonium hydroxide above, other bases can be utilized to form the metal salts, in addition or alternative to ammonium hydroxide, such as potassium hydroxide (KOH), sodium hydroxide (NaOH), etc.

In one particular embodiment, the core includes iron(II, III) oxide (e.g., $Fe_3O_4$), which is formed through coprecipitation of Fe(III) salts and Fe(II) salts. For example, the Fe(III) salts and Fe(II) salts can be present in a molar ratio of Fe(III) salts to Fe(II) salts of about 4:1 to about 1:1, such as about 2:1.

Other metal salts can be mixed with the iron salts to make mixed metal iron salts. Such salts may be magnetic or non-magnetic although it is recognized that non-magnetic materials will lower the magnetization properties of the resulting nanoparticles. For example, metals salts formed from metals such as cobalt, manganese, titanium, zinc, and tin can form mixed metal oxides with the iron oxides.

The metal salts are generally precipitated at a precipitation temperature that is less than the boiling point of the solvent. For example, when the solvent includes water, the precipitation temperature is less than 100° C., such as about 75° C. to about 99° C. (e.g., about 80° C. to about 95° C., such as about 85° C. to about 95° C.) resulting in iron oxide nanoparticles being formed.

In particular embodiments, oleic acid can be added in a slow, relatively constant manner (e.g., dropwise) shortly after particle precipitation (e.g., about 30 minutes to about 3 hours, such as about 1 hour, after particle precipitation). The resulting solution can then be stirred at the precipitation temperature for a sufficient time to stabilize the particles (e.g, about 1 to about 5 hours, such as about 2 hours).

An oxide shell can then be formed on the metal oxide core. In one embodiment, the oxide shell can be a silicon oxide shell, such as formed by hydrolyzation of tetraethyl orthosilicate to form silicon oxide on the metal oxide core. Other metal oxides and metal salts can be mixed with the silicates to prepare mixed metal silicates such zirconium oxide, titania, and lanthanide oxides.

Through these methods, core-shell magnetic nanoparticles can be formed to have an average diameter of about 1 nm to about 500 nm, such as about 5 nm to about 100 nm (e.g., about 5 nm to about 25 nm). For $Fe_3O_4$ nanoparticles, the saturation magnetization is dependent on the size of the particles. Generally, the smaller the particles, the lower the saturation magnetization value due to the surface spin canting effect. And the saturation magnetization is low when particles are smaller than 10 nm. Of particular advantage, magnetic nanoparticles formed according to the presently presented process can still maintain high magnetization with a size around 10 nm, which was not possible with other methods.

Additionally, the resulting core-shell magnetic nanoparticles have a relatively high saturation magnetization, which was quantified via vibrating sample magnetometer (VSM). For many applications requiring high saturation magnetization, values of about 20 to about 80 emu/g, or more preferably about 40 to about 80 emu/g are desirable.

II. Attaching an Anchoring Compound to the Magnetic Nanoparticles

After formation of the core-shell magnetic nanoparticles, an anchoring agent can be attached to the magnetic nanoparticle. Generally, the anchoring agent comprises a functional group allowing the attachment of further molecules thereto.

In one embodiment, the functional group of the anchoring agent comprises an amine functional group, such as a primary amine functional group (i.e., —$NH_2$). For example, an amino silane agent (e.g., 3-aminopropyldimethylethoxysilane) can be added to nanoparticles dispersed in a solvent (e.g., dry DMF or THF). The reaction mixture can then be stirred at a reaction temperature (e.g., about 50° C. to about 90° C., such as about 75° C.) in an inert atmosphere (e.g., $N_2$) for a sufficient time to react the siloxane function group to the nanoparticles.

Other functional groups could also be attached that are useful for further attachment, such as amino groups, carboxylic acid groups, bromo groups, azido groups, alkene groups, alkyne groups, thiol groups, alcohol groups, or pentafluorophenyl groups. For example, a carboxylic acid group can be attached through reacting the amino functional group with succinic acid via a ring opening reaction. Alternatively, a bromo group can be attached through reaction of 3-bromopropyltrimethoxysilane with the nanoparticles in dry THF at a reaction temperature (e.g., about 75° C.). An azido group group can be attached by further reacting the bromo group functionalized nanoparticles with sodium azide in DMF/H2O mixture at a reaction temperature (e.g., about 80° C.). In yet another alternative, an alkyne group can be attached by reacting the above amino functional groups with 4-pentynoic acid at a reaction temperature (e.g., room temperature) in dry THF.

III. RAFT Functionalization of the Core-Shell Magnetic Nanoparticles

Optionally, a RAFT agent can be reacted with the functional group of the anchoring agent such that the RAFT agent is bonded to the magnetic nanoparticle through the anchoring agent. Almost all the RAFT agents containing acid functional group are suitable for this reaction, such as broad categories of dithioesters, trithiocarbonates, and xanthantes. In certain embodiments, the reaction conditions for activating the acid containing RAFT agents with 2-mercaptothiazoline can be performed at room temperature in a dry organic solvent for about 4 to about 6 hours. Then, the activated RAFT agents can easily react with nanoparticle anchored amino groups to achieve the surface attachment.

IV. RAFT Polymerization

Generally, Reversible Addition-Fragmentation chain Transfer (RAFT) polymerization is one type of controlled radical polymerization. RAFT polymerization uses thiocarbonylthio compounds, such as dithioesters, dithiocarbamates, trithiocarbonates, and xanthates, in order to mediate the polymerization via a reversible chain-transfer process. RAFT polymerization can be performed by simply adding a chosen quantity of appropriate RAFT agents (thiocarbonylthio compounds) to a conventional free radical polymerization. RAFT polymerization is particularly useful with monomers having a vinyl functional group (e.g., a (meth)acrylate group and styrenics).

Typically, a RAFT polymerization system includes the monomer, an initiator, and a RAFT agent (also referred to as a chain transfer agent). Because of the low concentration of the RAFT agent in the system, the concentration of the initiator is usually lower than in conventional radical polymerization. Suitable radical initiators can be azobisisobutyronitrile (AIBN), 4,4'-azobis(4-cyanovaleric acid) (ACVA), etc.

RAFT agents are generally thiocarbonylthio compounds (or as more broadly defined, see earlier comment), such as generally shown below:

RAFT agent where the z group primarily stabilizes radical species added to the C=S bond and the R group is a good homolytic leaving group which is able to initiate monomers. The z and R" group of a RAFT agent is chosen according to a number of considerations. The Z group primarily affects the stability of the S=C bond and the stability of the adduct radical (polymer-S—C.(Z)—S-polymer), which, in turn, affect the position of and rates of the elementary reactions in the pre- and main-equilibrium. The R" group stabilizes a radical such that the right hand side of the pre-equilibrium is favored, but remains unstable enough that it can reinitiate growth of a new polymer chain.

As stated, RAFT is a type of living polymerization involving a conventional radical polymerization in the presence of a reversible chain transfer reagent. Like other living radical polymerizations, the termination steps are minimized in the RAFT process. The reaction is started by radical initiators (e.g., AIBN). In this initiation step, the initiator reacts with a monomer unit to create a radical species which starts an active polymerizing chain. Then, the active chain reacts with the thiocarbonylthio compound, which produces the homolytic leaving group (R"). This is a reversible step, with an intermediate species capable of losing either the leaving group (R") or the active species. The leaving group radical then reacts with another monomer species, starting another active polymer chain. This active chain is then able to go through the addition-fragmentation or equilibration steps. The equilibration keeps the majority of the active propagating species into the dormant thiocarbonyl compound, limiting the possibility of chain termination. Thus, active polymer chains are in equilibrium between the active and dormant species. While one polymer chain is in the dormant stage (bound to the thiocarbonyl compound), the other is active in polymerization.

By controlling the concentration of initiator and thiocarbonylthio compound and/or the ratio of monomer to thiocarbonylthio compound, the molecular weight of the polymeric chains can be controlled with low polydispersities.

Depending on the target molecular weight of final polymers, the monomer to RAFT agent ratios can range from about less than about 10 to more than about 1000 (e.g., about 10 to about 1,000). Other reaction parameters can be varied to control the molecular weight of the final polymers, such as solvent selection, reaction temperature, and reaction time. For instance, solvents can include conventional organic solvents such as tetrahydrofuran, toluene, dimethylformamide, dimethylacetamide, anisole, acetonitrile, dichloromethane, etc. The reaction temperature can range from room temperature (e.g., about 20° C.) to about 120° C. The reaction time can be from less than about 1 h to about 48 h.

The RAFT process allows the synthesis of polymers with specific macromolecular architectures such as block, gradient, statistical, comb/brush, star, hyperbranched, and network copolymers.

Because RAFT polymerization is a form of living radical polymerization, it is ideal for synthesis of block copolymers. For example, in the copolymerization of two monomers (A and B) allowing A to polymerize via RAFT will exhaust the monomer in solution with significantly suppressed termination. After monomer A is fully reacted, the addition of monomer B will result in a block copolymer. One requirement for maintaining a narrow polydispersity in this type of copolymer is to have a chain transfer agent with a high transfer constant to the subsequent monomer (monomer B in the example).

In the present method, a plurality of monomers can be polymerized on the RAFT agent attached to the nanoparticle to form a polymeric chain covalently bonded to the magnetic nanoparticle via the RAFT agent. Two methods can be utilized to form the polymeric chain extending from the nanoparticles via the attached RAFT agent: a "grafting-from" approach and a "grafting-to" approach. These strategies will be explained in more details in the following sections. See also, U.S. Publication No. 2013/0041112 of Benicewicz, et al.; U.S. Publication No. 2012/0302700 of Tao, et al.; and international patent application publication no. WO/2013/078309 of Benicewicz, et al., the disclosures of which are incorporated by reference herein.

A. "Grafting-From" Methods

In one embodiment, the polymeric chain can be formed by RAFT polymerization of a plurality of monomers on the attached RAFT agent, resulting in the polymeric chain being covalently bonded to the nanoparticle via the RAFT agent. The particular types of monomer(s) and/or RAFT polymerization conditions can be selected based upon the desired polymeric chain to be formed. For example, monomers containing acrylate, methacrylate groups, acrylamides, styrenics, etc., are particularly suitable for formation of the polymeric chain.

Thus, the "grafting-from" method involves formation of the polymeric chain onto the attached RAFT agent and results in the polymeric chain being covalently bonded to the nanoparticle via the attached RAFT agent.

B. "Grafting-To" Methods

In one embodiment, the polymeric chain can be first polymerized via RAFT polymerization with a RAFT agent and subsequently covalently bonded directly to the surface of the nanoparticle, via the functional group of the attached anchoring compound. Thus, in this embodiment, the polymeric chain has been polymerized prior to attachment to the nanoparticle's surface.

Alternatively, the polymeric chain can be first polymerized and subsequently covalently bonded to the surface of the nanoparticle, via a RAFT agent attached to the surface of the nanoparticle via the anchoring compound. Thus, in this embodiment, the first polymeric chain has been polymerized prior to attachment to the first anchoring compound. In this embodiment, the first polymeric chain is not limited to the type of polymerization and/or types of monomer(s) capable of being polymerized directly to the attached RAFT agent. As such, as long as the polymeric chain defines a functional group that can react and bond to the attached RAFT agent, any polymeric chain can be bonded to the nanoparticle.

V. Responsive Polymeric Chains

In one particular embodiment, a pH responsive polymeric chain can be attached to the core-shell magnetic nanoparticle. For example, poly(methacrylic acid) (PMAA) and other polymers made from acid-containing monomers represent an important class of stimuli-responsive polymers and have been widely used in membrane transport, biomedical applications, coatings, and sensors. There are few reports about the synthesis of PMAA or other multi-acid-containing polymers on nanoparticle surfaces using deprotection of the tertiary butyl protecting groups of poly(tert-butylacrylate) or poly(tert-butylmethacrylate). Nobody has conducted direct surface-initiated RAFT polymerization of methacrylic acid or other acid containing monomers on small nanoparticle surfaces. One particular challenge is maintaining good dispersibility of the polymer grafted nanoparticles using small size substrate nanoparticles. Generally, smaller size nanoparticles agglomerate more readily than larger particles. Thus, the size and nature of the substrate nanoparticles are important issues affecting the final dispersibility of polymer grafted nanoparticles.

In one embodiment, direct polymerization of MAA on small diameter magnetic nanoparticles (as small as 10 nm) in a controlled manner via surface-initiated RAFT polymerization is generally provided herein. The multi carboxylic acid moieties provide an important and classic organic synthesis precursor for post functionalization with targeting compounds. In addition, the incorporation of fluorescent dye molecules on magnetic nanoparticles provide universal imaging probes and would be helpful in monitoring the presence and movement of particles in biological cells or other systems.

VI. Magnetic Nanoparticles as Drug Delivery Vehicles

The growing phenomenon of bacterial resistance to antibiotics results in high morbidity and mortality, which is an exceptionally urgent healthcare problem. A wide range of antibiotics, such as penicillin, have become ineffective or have limited effectiveness against bacteria since their first usages decades ago. Magnetic nanoparticles with a series of advantages, such as high surface to volume ration, magnetic properties, and unique nano-size effects, have been employed as drug delivery vehicles. They have been widely used to carry and release active biomolecules to eukaryote cells, however, there are few reports regarding use of magnetic nanoparticles to carry and release active biomolecules to target bacteria. Furthermore, the recyclability of magnetic nanoparticles in bacterial systems has not been reported.

In one embodiment, polymeric chains attached to a core-shell magnetic nanoparticle via RAFT polymerization according to the foregoing description can be conjugated to one or more bacterial resistant antibiotic agents (e.g., penicillin). In particular, this conjugation can include the non-covalent attachment (e.g., via ionic bonding, hydrogen bonding, van der Waals forces, etc.) of an antibiotic to the polymeric chains. For example, penicillin can be physically attached to PMAA grafted magnetic nanoparticles.

In one embodiment, an antibiotic can exhibit enhanced antimicrobial activity against bacteria when conjugated to a core-shell magnetic nanoparticle rather than as free antibiotic. Such bacteria can include, for example, *Escherichia coli* (Gram-negative) and/or *Staphylococcus aureus* (Gram-positive). In general, core-shell magnetic nanoparticles exhibit no activity to bacteria. Also, in general, the enhancement can be demonstrated by a variety of doses of the antibiotic.

The magnetic properties of a core-shell magnetic nanoparticle conjugated to an antibiotic allows for the nanoparticles to be directed in complicated bacterial environments. For example, core-shell magnetic nanoparticles conjugated to an antibiotic can be directed, due to their magnetic properties, in biofilms, while free antibiotic are not able to access cells in the sticky extracellular polymeric substances (EPS) of biofilms.

In one embodiment, a core-shell magnetic nanoparticle conjugated to an antibiotic can be recycled. Recycling a core-shell magnetic nanoparticle conjugated to an antibiotic can include removing the core-shell magnetic nanoparticle from a biological environment. In one embodiment, such a removal avoids pollution of the biological environment. For example, removing core-shell magnetic nanoparticles from a biological environment can avoid nano-based pollution. Pollution-free removal of a core-shell magnetic nanoparticle can be achieved by exploiting the magnetic properties of the core-shell magnetic nanoparticle. For example, the magnetic nanoparticles can be directed by a magnet to exit a substantially stationary biological environment. In another example, the magnetic nanoparticles can be held substantially stationary by a magnet while the biological environment is removed from where the nanoparticles are held, such as by holding the magnetic nanoparticles at the bottom of a container with a magnet while pouring a biological supernatant out of the container.

Recycling a core-shell magnetic nanoparticle conjugated to an antibiotic can also include detaching the antibiotic from the core-shell magnetic nanoparticle, which can subsequently be conjugated to fresh antibiotic. In one embodiment, after an antibiotic is detached from the core-shell magnetic nanoparticles, the core-shell magnetic nanoparticles are washed several times before fresh antibiotic is conjugated to the nanoparticles. In general, the fresh antibiotic exhibits enhanced antimicrobial activity against bacteria when conjugated to the recycled core-shell magnetic nanoparticle rather than as free antibiotic.

EXAMPLES

The $Fe_3O_4/SiO_2$ magnetic nanoparticles were synthesized by two methods.

The first strategy was a microemulsion method employing the mixing of two separate microemulsions (ME1 and ME2) resulting in the formation of nanoparticles. ME1 had Triton X-100, cyclohexane, n-hexanol, water, TEOS, $FeCl_3$ and $FeSO_4$, while ME2 contained Triton X-100, cyclohexane, n-hexanol, water, TEOS and the base ($NH_4OH$).

The generated $Fe_3O_4/SiO_2$ nanoparticle solution was light brown and transparent. The TEM image illustrated that the $Fe_3O_4/SiO_2$ nanoparticles were well dispersed and shows that the diameter of the individual nanoparticles was approximately 11 nm. The colors of the nanoparticles varied from dark brown to light yellow. The lighter color of the magnetic nanoparticles was observed in compositions containing higher amounts of TEOS. The nanoparticles with 10×TEOS usage have higher weight loss (18.6%) compared to the particles with 5×TEOS usage (17.3% weight loss) at 940° C. in TGA analysis. Increasing the proportion of TEOS would be helpful to enhance the $SiO_2$ part of the nanoparticles. Even though well-dispersed nanoparticles were obtained using the microemulsion method, the nanoparticles did not have high saturation magnetization (less than 5 emu/g) and strong magnetic responses, similar to other $Fe_3O_4/SiO_2$ magnetic nanoparticles. Thus, there was motivated to develop a new strategy to prepare $Fe_3O_4/SiO_2$ magnetic nanoparticles with high magnetization, excellent dispersity, and small size.

The second strategy was based on the coprecipitation of $Fe^{2+}$ and $Fe^{3+}$ salts in basic aqueous solutions at low temperature to form nanoparticles. Fe(III) and Fe(II) salts were coprecipitated with $NH_4OH$ at 90° C. to form iron oxide nanoparticles followed by the hydrolyzation of tetraethyl orthosilicate (TEOS) on the nanoparticle core to form $Fe_3O_4$—$SiO_2$ core-shell magnetic nanoparticles. The XRD pattern confirmed the non-crystalline $SiO_2$ shell ascribed to the broad peak at 10°-30° and the cubic spinel structure of $Fe_3O_4$ due to the strong diffraction peaks at 30.1°, 35.6°, 43.2°, 53.9°, 57.2, 62.8°, and 74.2° which were indexed to (220), (311), (400), (422), (511), (440) and (533) planes. The IR analysis of $Fe_3O_4$ confirmed the absorption peaks at 2924 $cm^{-1}$, 2854 $cm^{-1}$, and 1710 $cm^{-1}$ ascribed to the —$CH_2$ and C=O of $Fe_3O_4$ surface physically absorbed oleic acid respectively. The peak at 1409 $cm^{-1}$ revealed chemically bound oleic acid on $Fe_3O_4$ ascribed to the stretch of $COO^-$ resulting from the coordination with iron of $Fe_3O_4$. The IR spectra of $Fe_3O_4/SiO_2$ demonstrated the existence of $SiO_2$ after surface hydrolysis of TEOS on $Fe_3O_4$ nanoparticles based on the appearance of strong absorption peaks at 1135 $cm^{-1}$, 1056 $cm^{-1}$, 947 $cm^{-1}$ and 805 $cm^{-1}$. The magnetic nanoparticle solution was dark brown in solution and the generated nanoparticle powder after wash and dry was capable of lifting a medium size (1.5 cm diameter, 0.9 cm thickness) magnet off the ground, which qualitatively demonstrated the high magnetic moment of the new prepared magnetic nanoparticles. The Vibrating Sample Magnetometer (VSM) measurement demonstrated the superparamagnetivity of both $Fe_3O_4$ and $Fe_3O_4/SiO_2$ nanoparticles with a high magnetic moment of 59.5 emu/g and 29.1 emu/g, respectively. The silica coated nanoparticles possess a lower magnetic moment than the bare $Fe_3O_4$, which is known in the art. The TGA showed that the organic proportion in the $Fe_3O_4/SiO_2$ nanoparticles accounted for 35% by weight, while the organic proportion in the bare $Fe_3O_4$ nanoparticles accounted for only 24% by weight. The TEM image illustrates that both the $Fe_3O_4$ and $Fe_3O_4/SiO_2$ nanoparticles were well dispersed and mono-distributed. The average diameter of the $Fe_3O_4/SiO_2$ nanoparticles was around 10 nm. Compared to the traditional thermal decomposition of Fe(III) chelate in high boiling point solvent (>200° C.) strategy, this method is much more mild in operation conditions providing high-magnetization superparamagnetic nanoparticles with a small size.

That is, for $Fe_3O_4$ nanoparticles, the saturation magnetization is dependent on the size of the particles. Generally, the smaller particles, the lower saturation magnetization value due to the surface spin canting effect. And the saturation magnetization is low when particles are smaller than 10 nm. However, the magnetic nanoparticles of this example still maintained high magnetization with a size around 10 nm.

Table 1 shows the microemulsion method for preparation of $Fe_3O_4/SiO_2$ magnetic nanoparticles according to these Examples:

TABLE 1

| Group | Microemulsion | Surfactant (Triton X-100) | Solvent (oil) cyclohexane | Cosurfactant (n-hexanol) | Water | TEOS | $FeCl_3$ (0.15M) | $FeSO_4$ (0.1M) | $NH_4OH$ (29 wt. %) |
|---|---|---|---|---|---|---|---|---|---|
| A | ME1 | 5.3 mL | 22.5 mL | 5.4 mL | 620 μL | 10 μL | 500 μL | 500 μL | |
|   | ME2 | 5.3 mL | 22.5 mL | 5.4 mL | 810 μL | 10 μL | | | 810 μL |
| B | ME1 | 5.3 mL | 22.5 mL | 5.4 mL | 620 μL | 100 μL | 500 μL | 500 μL | |
|   | ME2 | 5.3 mL | 22.5 mL | 5.4 mL | 810 μL | 100 μL | | | 810 μL |
| C | ME1 | 5.3 mL | 22.5 mL | 5.4 mL | 620 μL | 50 μL | 500 μL | 500 μL | |
|   | ME2 | 5.3 mL | 22.5 mL | 5.4 mL | 810 μL | 50 μL | | | 810 μL |
| D | ME1 | 5.3 mL | 22.5 mL | 5.4 mL | 620 μL | 10 μL | 1000 μL | 1000 μL | |
|   | ME2 | 5.3 mL | 22.5 mL | 5.4 mL | 810 μL | 10 μL | | | 810 μL |
| E | ME1 | 5.3 mL | 22.5 mL | 5.4 mL | 1240 μL | 10 μL | 500 μL | 500 μL | |
|   | ME2 | 5.3 mL | 22.5 mL | 5.4 mL | 1620 μL | 10 μL | | | 810 μL |

Figure 1:
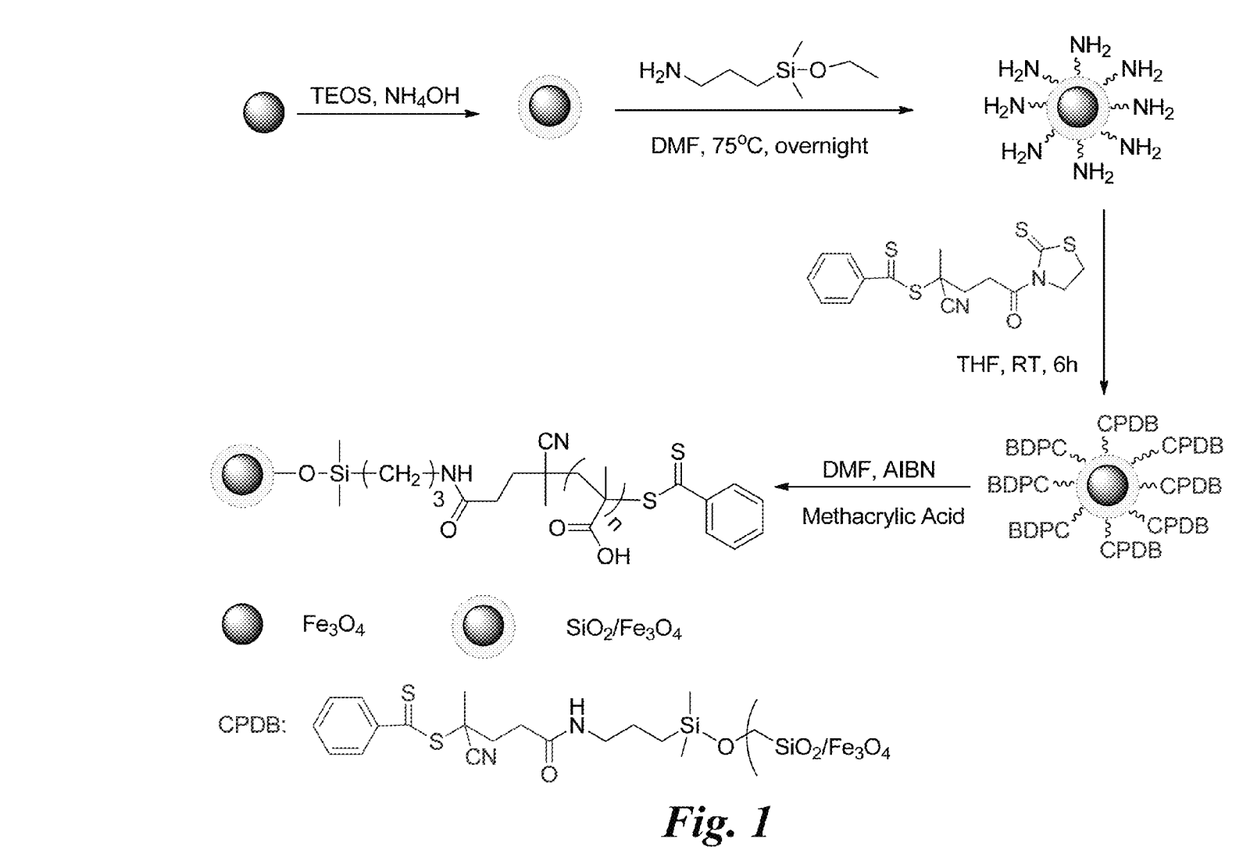
FIG. 1 shows a synthetic scheme for preparation of PMAA grafted $Fe_3O_4/SiO_2$ nanoparticles via direct polymerization of MAA, according to the Examples.
Figure 2:
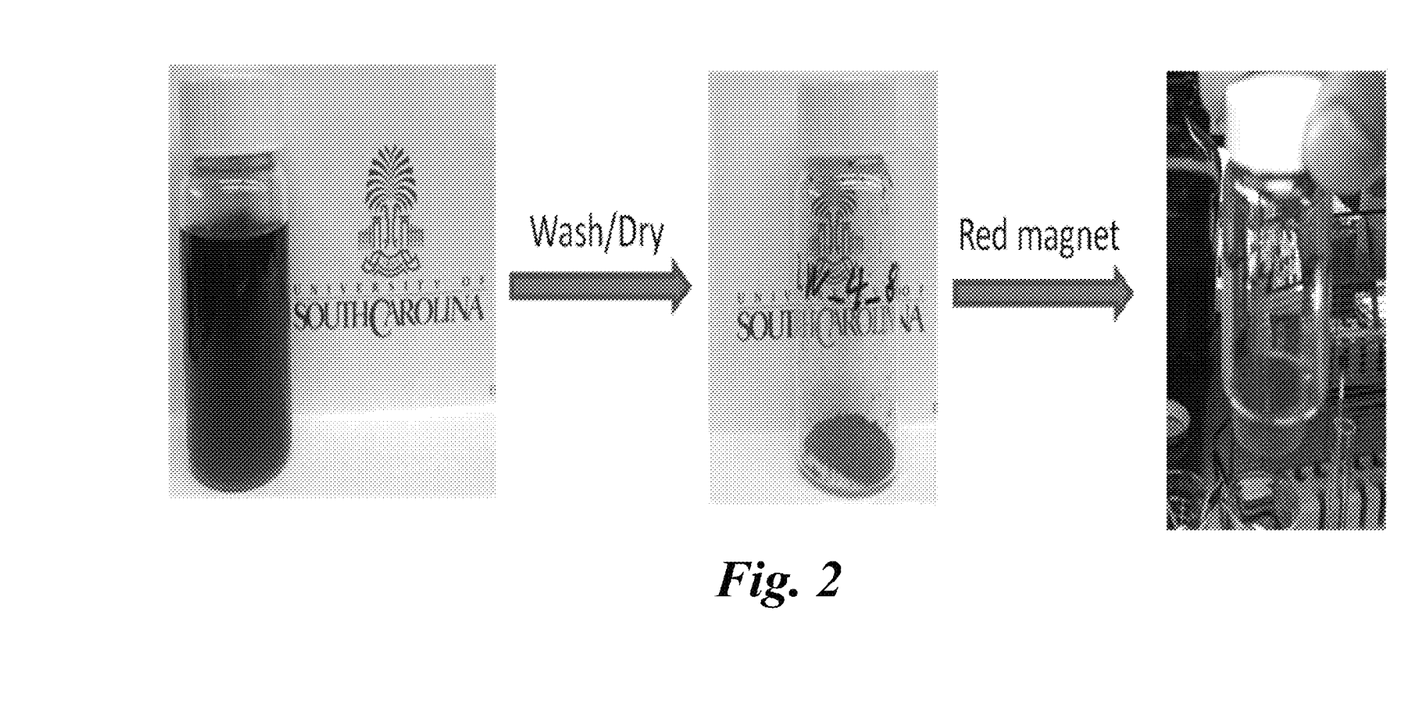
FIG. 2 shows photographs of the magnetic nanoparticles formed according to the Examples attract a medium size red magnet off the ground.
Figure 3:
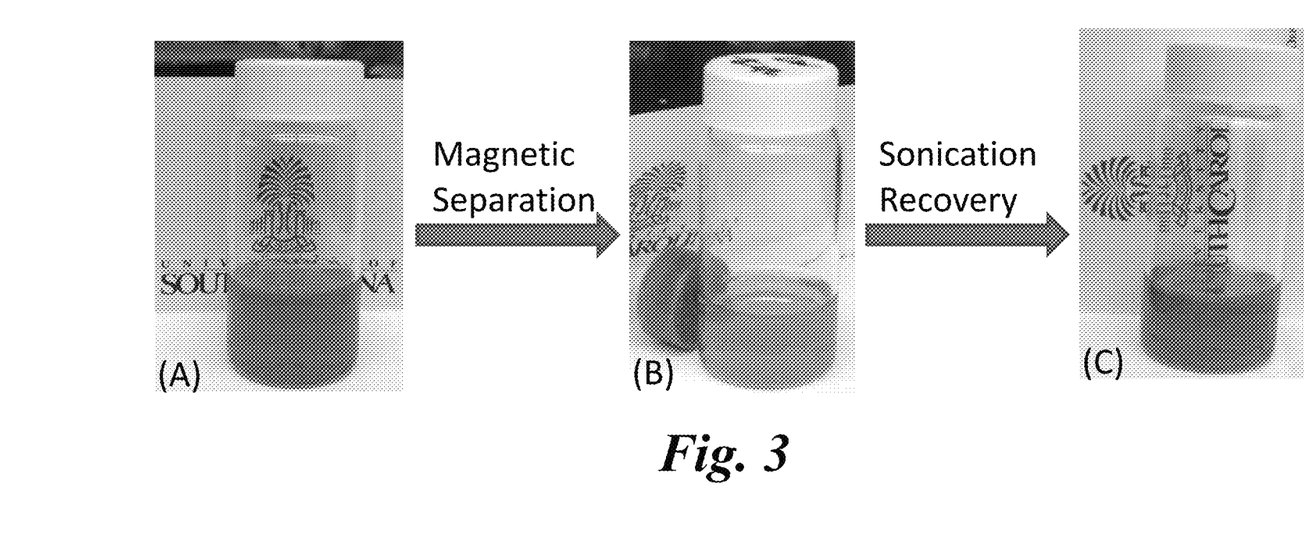
FIG. 3 shows PMAA grafted $Fe_3O_4/SiO_2$ nanoparticles in DMF according to the Examples: (A) in a normal state; (B) after magnetic separation; and (C) after sonication recovery 14 days later.

The strategy for preparation of PMAA grafted $Fe_3O_4/SiO_2$ magnetic nanoparticles is shown in FIG. 1. Amino coated $Fe_3O_4/SiO_2$ nanoparticles were prepared by the reaction between the $Fe_3O_4/SiO_2$ nanoparticles and 3-aminopropyldimethylethoxysilane. The RAFT agent coated $Fe_3O_4/SiO_2$ nanoparticles were synthesized by allowing the amino coated $Fe_3O_4/SiO_2$ nanoparticles with precisely determined densities to react with an excess of activated 4-cyanopentanoic acid dithiobenzoate (CPDB). This method generated a universal platform for surface initiated RAFT polymerization of nanoparticles with magnetic properties. The CPDB covalently bound to the nanoparticle surface was confirmed via UV-vis absorption at 305 nm. Then, the surface-initiated RAFT polymerization of MAA was conducted in DMF to generate PMAA brushes grafted onto magnetic nanoparticles.

Surface-initiated RAFT polymerization of MAA directly on $Fe_3O_4/SiO_2$ nanoparticles was conducted in DMF at 65° C. with a ratio between species of [MAA]:[CPDB]:[AIBN] =1000:1:0.1. The PMAA grafted $Fe_3O_4/SiO_2$ nanoparticles were methylated by trimethylsilyldiazomethane followed by cleavage of the methylated chains from the nanoparticle surface with hydrofluoric acid solution to conduct accurate measurement of the molecular weights via organic phase (THF) GPC characterization. The IR analysis of the nanoparticles confirmed the presence of the strong absorption peak at ~2951 $cm^{-1}$ ascribed to the methyl moiety after methylation. In addition, the absence of a broad peak at 3500~2500 $cm^{-1}$ ascribed to the hydroxyl group in —COOH and the shift of the carbonyl stretch peak from 1700 $cm^{-1}$ to 1729 $cm^{-1}$ confirmed the methylation of the anchored PMAA chains. The TGA demonstrated that the surface anchored PMAA accounted for 80% by weight. The PMAA grafted $Fe_3O_4/SiO_2$ nanoparticle solution was brown and transparent in DMF. The magnetic nanoparticles had a strong magnetic responsive property and could be easily redispersed in DMF after sonication maintaining the excellent dispersity in solution for at least 2 weeks. The grafted magnetic nanoparticles also readily dispersed in water. The TEM image revealed that the PMAA grafted $Fe_3O_4/SiO_2$ hybrid nanoparticles were well dispersed, and showed that the size of the individual nanoparticles was around 40-50 nm, which was consistent with the AFM image.

The PMAA grafted magnetic nanoparticles were used to non-covalently attach the beta-lactam antibiotic penicillin-G (PenG) and subsequently tested for activity against bacteria. *Escherichia coli* (Gram-negative) and *Staphylococcus aureus* (Gram-positive) were selected as the target bacteria. The disk diffusion assay of PenG-nanoparticle complex was conducted with a control group of free PenG of the same dose (12 μg PenG). In addition, as another control group, unloaded PMAA grafted magnetic nanoparticles demonstrated no activity (toxicity) to the target bacteria. The inhibition zone diameter of free PenG was 18 mm while the inhibition zone diameter of PenG-nanoparticle complex was 23 mm (27.8% increase), which demonstrated that nanoparticle conjugated PenG possessed enhanced antimicrobial activity against *Staphylococcus aureus*. For *Escherichia coli*, similar trends were also observed using a variety of PenG doses. Thus, PMAA grafted magnetic nanoparticles enhanced the bioactivity of penG against bacteria when the nanoparticles were physically bound with PenG. Without wishing to be bound by any particular theory, it is believed that the enhanced inhibition activity was due to the locally high concentrations of antibiotics physically attached to PMAA grafted magnetic nanoparticles, which overwhelms the resistance of bacterial strains. The magnetic properties also offer a valuable stimulus technique to direct the nanoparticles in complicated bacterial environments, such as biofilms, while free antibiotic are not able to access cells in the sticky extracellular polymeric substances (EPS) of biofilms.

The culture solution method was used to evaluate the recyclability of PMAA grafted magnetic nanoparticles for antibiotic delivery and their activity against bacteria. As a control group, the unloaded PMAA grafted magnetic nanoparticles exhibited no activity to *E. coli* at the experimental conditions. The PenG-nanoparticle complex was added to the tryptic soy broth based *E. coli* culture solution with shaking at 37° C. After overnight incubation, the bacterial growth of the suspension was determined by recording absorbance at $OD_{600}$, and was compared to the standard bacterial culture solution without PenG and nanoparticles. Another control group of free PenG was tested in the same manner.

Figure 4:
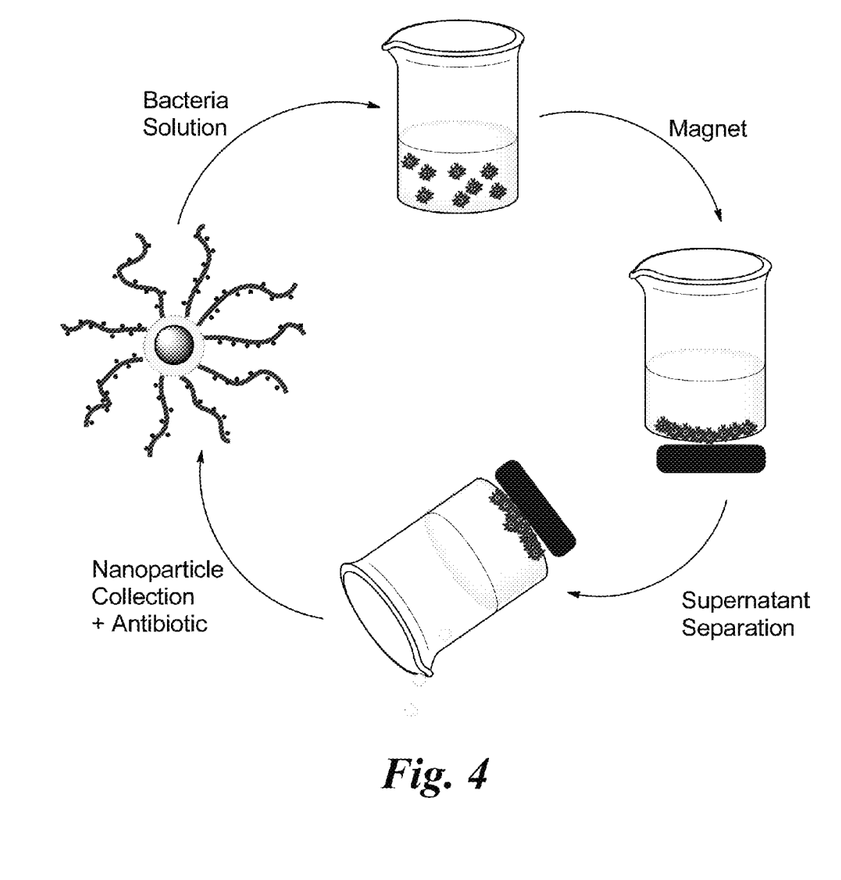
FIG. 4 shows a scheme of recycling magnetic nanoparticles to conjugate antibiotics for killing bacteria.

The PMAA grafted magnetic nanoparticles were extracted and recycled using a magnet, as shown in FIG. 4.

Figure 5:
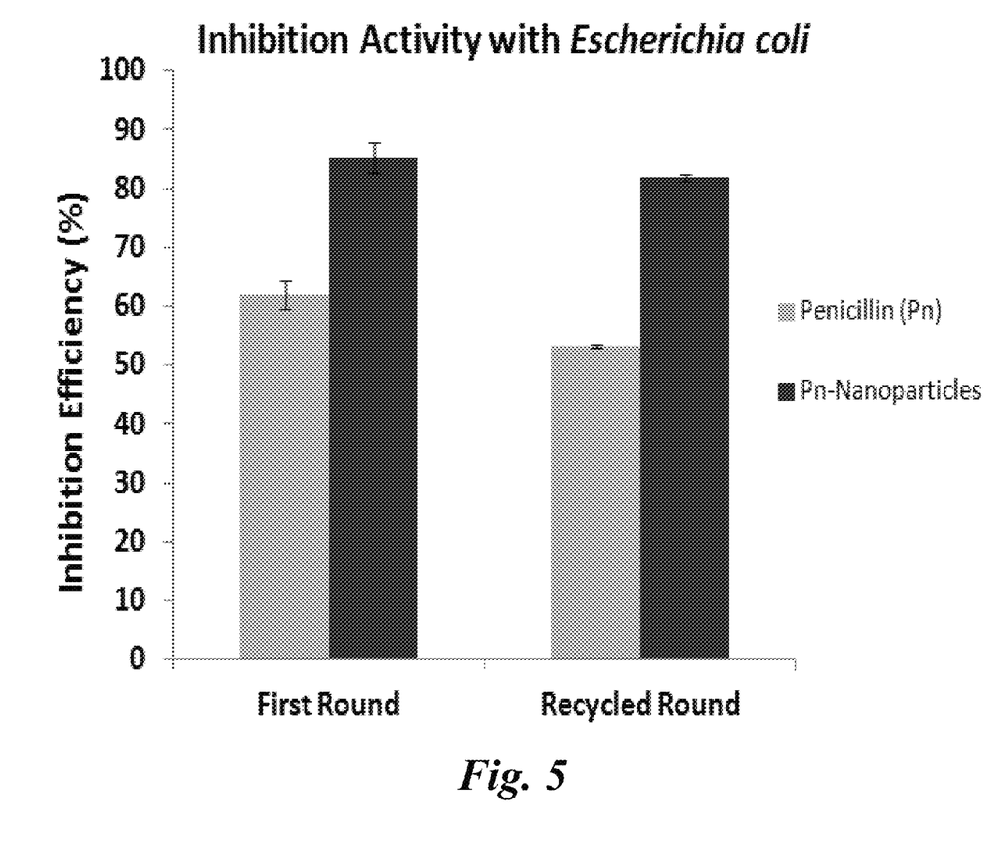
FIG. 5 shows a graph of the inhibition activities of free-PenG (left bars), and PenG complexed to carboxylated polymers on magnetic nanoparticles (right bars) as tested by bacterial culture solution with *E. coli* according to the Examples.

The nanoparticles were attracted at the bottom of the tube via a magnet and the supernatant was removed. The collected nanoparticles were washed several times and used again to bind PenG and tested again for their ability to kill bacteria employing the above mentioned method (FIG. 4). The enhanced inhibition efficiency of PenG-nanoparticle complex using the recycled magnetic nanoparticles was retained, which again was much higher than the free PenG (FIG. 5). Similar to the previous testing protocol, the two groups had same amount of PenG. It is postulated the effect is due to the locally high concentrations of PenG bound to nanoparticles, which increases the effectiveness of the PenG to overcome bacterial resistance.

In conclusion, an effective method for the preparation of $Fe_3O_4/SiO_2$ superparamagnetic nanoparticles with sizes as low as 10 nm and a high saturation magnetization using very mild synthetic conditions was demonstrated. CPDB coated $Fe_3O_4/SiO_2$ magnetic nanoparticles were prepared by treating amino functionalized $Fe_3O_4/SiO_2$ nanoparticles with activated CPDB. The direct surface-initiated RAFT polymerization of MAA was conducted on very small size $Fe_3O_4/SiO_2$ superparamagnetic nanoparticles while maintaining good dispersibility in solutions. The synthesis of the magnetic nanoparticle was confirmed by FTIR, TGA, VSM, TEM and AFM. The PMAA grafted $Fe_3O_4/SiO_2$ magnetic nanoparticles enhanced the bioactivity of PenG over bacteria (*Staphylococcus aureus* and *Escherichia coli*) when physically bound with PenG. The particles were removed from water solutions using a magnet after antimicrobial testing, thus avoiding nano-based pollution of the biological environment. The recycled PMAA grafted magnetic particles retained excellent aqueous phase dispersibility and high biological activity against bacteria when loaded with fresh PenG. The small size PMAA grafted magnetic nanoparticles with precisely controllable surface polymer brush lengths and PDIs provide an important platform to restore the activities of ineffective antibiotics via a new combination of materials to overcome bacterial resistance. The water-soluble PMAA grafted $Fe_3O_4/SiO_2$ magnetic nanoparticles may also find broad applications in MRI, and multiple drug delivery and therapeutic fields.

Experimental

Synthesis of $Fe_3O_4/SiO_2$ Magnetic Nanoparticles

1) Synthesis of Iron Oxide Nanoparticles: 6.94 g $FeCl_3$ and 6.04 g $FeSO_4 \cdot 7H_2O$ were dissolved in 400 mL $N_2$ purged DI water. 15 mL 29 wt % $NH_4OH$ was added slowly to the stirring solution at 90° C. under $N_2$ protection. Then 9 mL oleic acid was added dropwise 1 hour later and the resulting solution was stirred at 90° C. for 2 hours. The solution was precipitated into a large amount of acetone to remove extra oleic acid.

2) Synthesis of Silica Coated Iron Oxide Nanoparticles: 2.5 mL Triton X-100 and 42 mL cyclohexane were added to a 250 mL round-bottom flask. After sonication for 1 min, 1-mL cyclohexane solution of $Fe_3O_4$ with a concentration of 22.4 mg/mL and 350 µL 29 wt % $NH_4OH$ were added slowly to the stirring solution at room temperature (RT). TEOS was added slowly and the resulting solution was stirred at RT for 18 hours. The final solution was washed with methanol to remove the surfactant by precipitation and centrifugation at 4000 rpm for 5 min, which was repeated 4 times.

Synthesis of Amino-Functionalized $Fe_3O_4/SiO_2$ Magnetic Nanoparticles 3-aminopropyldimethylethoxysilane (1.29 g, 8.0 mmol) was added to $Fe_3O_4/SiO_2$ nanoparticles (approx. 112 mg) dispersed in dry DMF (15 mL). The reaction mixture was stirred at 75° C. overnight under $N_2$ protection. The solution was precipitated into diethyl ether (200 mL), centrifuged at 3000 rpm for 5 minutes, redispersed in dry THF. The solution was precipitated again into hexane and redispersed in dry THF for further use.

Synthesis of CPDB-Functionalized $Fe_3O_4/SiO_2$ Magnetic Nanoparticles

Activated CPDB (202.4 mg, 532 mmol) was dissolved in dry THF (10 mL). The above amino-functionalized nanoparticles (approx. 110 mg, in 20 mL THF) were added slowly and the resulting solution was stirred at RT overnight. After the reaction, the solution was precipitated into cyclohexane and ethyl ether mixture. (200 mL, cyclohexane:ethyl ether=4:1), centrifuged at 3000 rpm for 5 minutes, redispersed in dry DMF. The solution was precipitated again into ethyl ether and redispersed in dry DMF. This procedure was repeated several times until the supernatant solution was colorless after centrifugation. The final nanoparticles were dispersed in dry DMF for further usage and an aliquot of the nanoparticles was subjected to UV-vis analysis to determine the graft densities of the coated CPDB on the particle surface.

Surface-Initiated RAFT Polymerization of Methacrylic Acid from CPDB Anchored $Fe_3O_4/SiO_2$ Nanoparticles.

Methacrylic acid (0.99 mL, $1.17 \times 10^{-2}$ mol), CPDB coated $Fe_3O_4/SiO_2$ nanoparticles (17 mg, 685.8 µmol/g) and dry DMF (2.88 mL) were added to a 20 mL Schlenk tube. After sonication for 1 min, AIBN (233 µL, 5 mM in DMF) was added. The solution was degassed by four freeze-pump-thaw cycles, filled with nitrogen, and then placed in an oil bath of 65° C. for various intervals. The polymerization was stopped by quenching in ice water.

Synthesis of PenG-Nanoparticle Complex

To prepare the PenG-nanoparticle complex, 33 µl of PMAA grafted nanoparticles (35 mg/ml) was added to 500 µl of Penicillin solution (1 mg/ml), followed by an incubation at 25° C. with shaking (280 rpm) for 2 hours. The resulting PenG-nanoparticle complex was collected via Amicon centrifuge tubes after the centrifugation at 10,000 rpm for 6 minutes. The complex was collected, re-suspended and washed via the centrifugation. The un-bound PenG amounts in the supernatant were negligible in the UV-vis analysis. Therefore, it was assumed that the majority of the PenG was conjugated to PMAA grafted nanoparticles.

Disk Diffusion Assay

*Escherichia coli* ATCC 25922 and *Staphylococcus aureus* ATCC 25423 were allowed to grow in 10 mL of tryptic soy broth (TSB) at 37° C. overnight to an optical density of 0.8 ($OD_{600}$=0.8) and then diluted 10-fold. 0.1 mL of the diluted culture was used to inoculate an agar plate. 6 mm disks were put on the plate surface, and then a free PenG or PenG-nanoparticle complex DMSO solution (30 µL) was added to the disks at different concentrations. The plates were allowed to incubate at 35° C., and the clear zone surrounding a disk represents the areas that bacteria were killed. Each test was conducted in duplicate.

Bacteria Inhibition Efficiency Determination

10 µl of *E. coli* suspensions (stock solutions, $OD_{600}$=0.8) were inoculated into 2 mL TSB solutions at 37° C. for incubation at 300 rpm overnight. Three tubes of the same bacterial culture solutions were prepared. Tube 1 was used as blank group without adding any PenG or nanoparticles.

Tube 2 was employed to test the activity of free PenG. 50 μl of PenG-nanoparticle complex (3.52 mg) was added to Tube 3 before incubation. Bacterial growth was measured at $OD_{600}$, and was compared to the Tube 1. Thus, the inhibition efficiency was calculated as follows: inhibition efficiency (%)=(Sample $OD_{600}$/Background $OD_{600}$)×100. The Background $OD_{600}$ was determined from Tube 1. Each test was conducted in duplicate.

CONCLUSION

In conclusion, iron oxide/silica core-shell magnetic nanoparticles with a high saturation magnetization were synthesized using a new method under mild operation conditions which is easy for scale-up production in industry. The responsive PMAA grafted magnetic nanoparticles have been synthesized using the direct surface-initiated RAFT polymerization techniques, which is straightforward without further chemical cleavages of the protecting groups issues. This invented technique for the fabrication of the responsive PMAA grafted magnetic nanoparticles provides a great universal platform for biomedical applications, such as magnetic resonance imaging (MRI), drug delivery and therapy.

The PMAA grafted magnetic nanoparticles enhanced the bioactivity of an antibiotic over bacteria when physically bound with the antibiotic. The PMAA grafted magnetic nanoparticles bound with antibiotic were recycled, and the recycled PMAA grafted magnetic nanoparticles retained their enhanced bioactivity against bacteria when bound with fresh antibiotic. The invented technique for utilizing PMAA grafted magnetic nanoparticles bound with antibiotic provides a platform for restoring the activities of ineffective antibiotics to overcome bacterial resistance, and the invented technique for recycling of PMAA grafted magnetic nanoparticles provides a platform for avoiding nano-based pollution of biological environments.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming core-shell magnetic particles, the method comprising:
forming an oxide shell around a metal oxide core to form a core-shell magnetic particle, wherein the metal oxide core comprises an iron oxide;
attaching an anchoring agent to the magnetic particle, wherein the anchoring agent comprises a functional group;
reacting a reversible addition-fragmentation chain transfer (RAFT) agent with the functional group of the anchoring agent such that the RAFT agent is bonded to the magnetic particle through the anchoring agent; and
attaching a polymeric chain to the RAFT agent.

2. The method of claim 1, further comprising:
non-covalently attaching an antimicrobial agent to the polymeric chain.

3. The method of claim 2, further comprising:
exposing bacteria to the core-shell magnetic particle.

4. The method of claim 3, further comprising:
recycling the core-shell magnetic particle.

5. The method of claim 1, wherein attaching the polymeric chain to the RAFT agent comprises:
polymerizing a plurality of monomers on the RAFT agent to form a polymeric chain covalently bonded to the magnetic particle via the RAFT agent.

6. The method of claim 1, wherein reacting a RAFT agent with the functional group of the anchoring agent such that the RAFT agent is bonded to the magnetic particle through the anchoring agent and attaching the polymeric chain to the RAFT agent comprises:
polymerizing a plurality of monomers to form the polymer chain with the RAFT agent attached; and
thereafter, attaching the polymeric chain to the particle surface via the RAFT agent.

7. The method as in claim 1, wherein the oxide shell comprises silicon oxide.

8. The method as in claim 1, wherein the oxide shell comprises silicon mixed with zirconium, titanium, or lanthanides.

9. The method as in claim 1, wherein the metal oxide core comprises iron mixed with cobalt, manganese, titanium, zinc, tin, or a combination thereof.

10. The method as in claim 1, wherein forming an oxide shell around a metal oxide core to form a magnetic nanoparticle comprises:
precipitating metal salts with a base to form the metal oxide core; and
hydrolyzation of tetraethyl orthosilicate on the metal oxide core to form an oxide shell on the metal oxide core, wherein the oxide shell comprises silicon oxide.

11. The method as in claim 10, wherein the base comprises $NH_4OH$, and wherein the metal salts comprise Fe(III) salts, Fe(II) salts, or a mixture thereof.

12. The method of claim 11, wherein the metal salts comprise a combination of Fe(III) salts and Fe(II) salts.

13. The method of claim 12, wherein the molar ratio of Fe(III) salts to Fe(II) salts is about 4:1 to about 1:1.

14. The method of claim 12, wherein the molar ratio of Fe(III) salts to Fe(II) salts is about 2:1.

15. The method as in claim 1, wherein the average diameter of the magnetic particle prior to attaching the anchoring compound is about 1 nm to about 500 nm.

16. The method as in claim 1, wherein the functional group of the anchoring agent comprises an amine functional group.

17. The method as in claim 1, wherein the RAFT agent comprises 4-cyanopentanoic acid dithiobenzoate.

* * * * *